United States Patent [19]

Funahashi et al.

[11] Patent Number: 4,876,363

[45] Date of Patent: Oct. 24, 1989

[54] EPOXY-CONTAINING ORGANIC SILICON COMPOUNDS

[75] Inventors: Yuichi Funahashi; Junichiro Watanabe; Kiyoshi Takeda; Makaoto Matsumoto, all of Ohta, Japan

[73] Assignee: Toshiba Silicone Co., Ltd., Japan

[21] Appl. No.: 238,720

[22] Filed: Aug. 30, 1988

[30] Foreign Application Priority Data

Sep. 11, 1987 [JP] Japan .................................. 62-226404

[51] Int. Cl.$^4$ .......................................... C07D 303/04
[52] U.S. Cl. .................................................. 549/215
[58] Field of Search ........................................ 549/215

[56] References Cited

U.S. PATENT DOCUMENTS 2,951,850  9/1960  Plueddemann ...................... 549/215
3,131,161  4/1964  Nitzsche et al. .................... 549/215
3,455,877  7/1969  Plueddemann ...................... 549/215

Primary Examiner—Richard L. Raymond
Assistant Examiner—Ba. K. Trinh

[57] ABSTRACT

Epoxy group-containing organic silicon compounds represented by general formula (I):

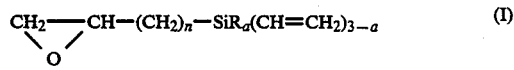

wherein R, which may be the same or different, each represents a monovalent hydrocarbon group free from an aliphatic unsaturated bond; a represents 1 or 2; and n represents an integer of 2 to 6. The epoxy-containing organic silicon compounds contain no hydrolyzable group therein and are suited for use in coupling of organic compounds and modification or crosslinking of polymers.

4 Claims, No Drawings

EPOXY-CONTAINING ORGANIC SILICON COMPOUNDS

The present application claims the priority of Japanese Patent Application Serial No. 62-226404 filed on Sept. 11, 1987.

BACKGROUND OF THE INVENTION

1. Field of the Invention

The present invention relates to novel organic silicon compounds. More particularly, the present invention relates to novel organic silicon compounds containing an epoxy group and a vinyl group bound to the silicon atom in the molecule thereof.

2. Statement of the Prior Art

Organic silicon compounds having two kinds of functional groups in the same molecule thereof are known and utilizing the reactivity of each functional group, they are used as silane coupling agents or as raw materials of or intermediates for various chemical substances, or the like. For example, organic silicon compounds used as silane coupling agents possess a carbon functional group capable of binding to an organic material and a silicon functional group capable of reacting with and binding to an inorganic material and are interposed at the interface between the organic material and the inorganic material to function to firmly bond both with each other.

However, hitherto known organic silicon compounds having two functional groups in the same molecule thereof are mostly those having a hydrolyzable group such as an alkoxy group as the silicon functional group. Where organic compounds are used to bond with each other the hydrolyzable silicon-oxygen-carbon bond remains in the product so that problems of poor moisture resistance, etc. may be encountered. Thus, there might be a limitation depending upon the purpose of use.

An object of the present invention is to provide novel epoxy-containing organic silicon compounds which are free from any hydrolyzable group in the molecule thereof and suited for use in coupling between organic compounds or modification or crosslinking, etc. of various organic compounds or polymers. As a result of extensive investigations with an attempt to obtain organic silicon compounds suited for the foregoing object, the present inventors have synthesized organic silicon compounds (I) having an epoxy group as a carbon functional group and a vinyl group bound to the silicon atom as a silicon functional group and have found that these organic silicon compounds are suited for the present purpose and, have come to accomplish the present invention.

The gist of the present invention lies in an epoxy-containing organic silicon compound represented by the general formula (I):

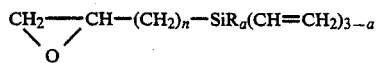
(I)

wherein each R, which may be the same or different, each represents a monovalent hydrocarbon group free from an aliphatic unsaturated bond; a represents 1 or 2; and n represents an integer of 2 to 6.

DETAILED DESCRIPTION OF THE INVENTION

R is a monovalent hydrocarbon group free from an aliphatic unsaturated bond and examples include various hydrocarbon groups, for example, an alkyl group such as methyl group, ethyl group, propyl group, butyl group, etc.; a cycloalkyl group such as cyclohexyl group; an aryl group such as phenyl group; an aralkyl group such as β-phenylethyl group or β-phenylpropyl group; etc. For easy accessibility and easy synthesis of raw materials as well as optimum heat stability of the silicon-containing high molecular compounds derived using the epoxy-containing organic silicon compounds of this invention, an alkyl group or phenyl group is preferred among the hydrocarbon groups which may be R. Particularly preferred is a methyl group since its handling is easy. When R is two or more, each monovalent hydrocarbon group may be different from each other or may be the same.

Symbol "a" is 1 or 2 but in view of easy synthesis, it is preferred to be 2.

Symbol "n" is an integer of 2 to 6. Compounds wherein n is 1 are poor in stability and are synthesized with difficulty.

The epoxy-containing organic silicon compound of the present invention can be obtained, for example, by reacting a halogen-containing organic silicon compound represented by general formula (II):

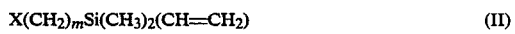
(II)

wherein X represents a halogen atom and m represents an integer of 1 to 5, with metallic magnesium in an ether solvent to synthesize a Grignard reagent represented by the general formula (III):

(III)

wherein X and m are as defined above, then reacting the Grignard reagent with epichlorohydrin in the presence of a monovalent copper salt to form a hydroxy-containing organic silicon compound represented by general formula (IV):

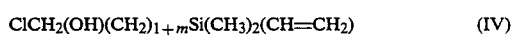
(IV)

wherein m is as defined above, and further cyclizing the hydroxy-containing organic silicon compound in a sodium hydroxide aqueous solution.

As is readily understood to one skilled in the art, it is evident that the use of the halogen-containing organic silicon compound of the general formula (II) wherein one or both of the two methyl groups bound to the silicon atom is/are replaced by other hydrocarbon group(s) (R) such as an ethyl group, phenyl group, etc. as the starting material gives other epoxy-containing organic silicon compounds of the present invention according to the reactions described above.

The organic silicon compound of the present invention possesses an epoxy group as the carbon functional group and a vinyl group bound to the silicon atom as the silicon functional group, in the molecule thereof and are thus useful as intermediates for organic synthesis as raw materials, of various chemical substances, raw materials of silicon-containing high molecular weight compounds or coupling agents between organic materials, etc., utilizing the reactivities of or difference in the reactivities between these functional groups.

The epoxy-containing organic silicon compound of the present invention has no hydrolyzable group in the molecule itself. Accordingly, using the epoxy-containing organic silicon compound as a starting raw material, an intermediate, a coupling agent, a modifier, etc., other organic silicon compounds having no hydrolyzable property, silicon-containing high molecular compounds, etc. can easily be obtained.

EXAMPLES

The present invention will be described in more detail by referring to the examples but is not deemed to be limited only to these examples. Parts and % are all by weight, unless otherwise indicated.

Example 1

To a flask equipped with a dropping funnel were charged 25.5 parts of magnesium for Grignard reagent and 500 parts of tetrahydrofuran. Then, 9.4 parts of 1,2-dibromoethane were charged therein. The mixture was stirred for 15 minutes. In a nitrogen flow, the temperature was raised to 70° C. an 135 parts of (chloromethyl)dimethylvinylsilane were dropwise added over 2 hours to prepare a Grignard reagent.

The reagent was diluted with 1,000 parts of tetrahydrofuran. At a temperature of 10° C., 1.9 parts of cuprous iodide were added. After stirring for 5 minutes, 92.5 parts of epichlorohydrin were dropwise added thereto over an hour. After completion of the dropwise addition, the temperature was elevated to 20° C. and stirring was continued for 30 minutes. Then, the mixture was cooled to 0° C. and 500 parts of a 1:1 mixture of n-hexane and diethyl ether and 300 parts of water were added to complete the reaction. Diluted hydrochloric acid was added until inorganic precipitates were dissolved. The organic phase was fractionated and collected. The organic phase was washed with saturated saline aqueous solution and then dried over magnesium sulfate. By distillation under reduced pressure, 158 parts of (4-chloro-3-hydroxybutyl) dimethylvinylsilane were obtained.

Next, 158 parts of the aforesaid reaction mixture, 250 parts of water and 117 parts of sodium hydroxide were charged in a flask. The temperature was elevated to 50° C. followed by stirring for 2 hours. Then, the mixture was cooled to room temperature and 100 parts of n-hexane were added to the mixture which was then fractionated the organic phase collected. The organic phase was washed with saturated ammonium chloride aqueous solution. After further washing with saturated aqueous saline solution, the system was dried over magnesium sulfate and distilled under reduced pressure to give 101 parts of the reaction product showing a boiling point of 50° C./2 Torr.

With respect to the reaction product, its molecular weight was determined by gas mass spectral anaylsis. Further elemental analysis was conducted and IR and ¹H-NMR spectra were determined. The results of these analyses and spectra are as shown in Table 1.

TABLE 1

| | |
|---|---|
| Molecular weight | 156 |
| Elemental analysis (%) | C 81.72 (61.48) |
| Figures with parenthesis | H 10.43 (10.32) |
| indicate calculated values. | Si 17.80 (17.97) |
| IR (liquid film method) | |
| $\nu$ (cm$^{-1}$) | 3030, 2945, 1245, 830, |

TABLE 1-continued

| | |
|---|---|
| | 512 |
| ¹H—NMR | 0.01 (S, 6H, Si(C$\underline{H}_3$)$_2$) |
| (90MHz; CCl$_4$) | 0.47–0.77 |
| δ (ppm) | (m, 2H, SiC$\underline{H}_2$CH$_2$—) |
| | 1.32–1.67 |
| | (m, 2H, SiCH$_2$C$\underline{H}_2$—) |
| | 2.22–2.65 |
| | (m, 2H, —C$\underline{H}$——C$\underline{H}_2$) with O bridge |
| | 2.62–2.85 |
| | (br, 1H, —C$\underline{H}$——CH$_2$) with O bridge |
| | 5.47–6.37 |
| | (m, 3H, Si—C$\underline{H}$=C$\underline{H}_2$) |

From the results of these analyses, it was verified that the obtained product was 3,4-epoxybutyl dimethylvinylsilane having the following structural formula.

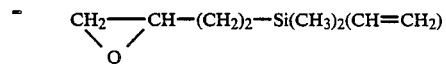

The yield to the theoretical yield was 65% based on (chloromethyl)dimethylvinylsilane.

Example 2

The reaction product showing a boiling point of 70° C./2.5 Torr was obtained in 100 parts in a manner similar to Example 1 except that 168 parts of (3-chloropropyl) dimethylvinylsilane was used in place of (chloromethyl)dimethylvinylsilane.

With the reaction product, identification was peformed as in Example 1. The results of these analyses and spectra are as shown in Table 2.

TABLE 2

| | |
|---|---|
| Molecular weight | 156 |
| Figures with parenthesis | H 11.03 (10.93) |
| indicate calculated values. | Si 15.07 (15.23) |
| IR (liquid film method) | |
| $\nu$(cm$^{-1}$) | 3040, 2930, 1245, 835 |
| ¹H—NMR | −0.03 (S, 6H, Si(C$\underline{H}_3$)$_2$) |
| (90MHz; CCl$_4$) | 0.35–0.68 |
| δ (ppm) | (br, 2H, SiC$\underline{H}_2$—) |
| | 1.12–1.62 |
| | (br, 6H, SiCH$_2$— C$\underline{H}_2$C$\underline{H}_2$CH$_2$—) |
| | 2.18–2.65 |

TABLE 2-continued (m, 2H, —CH——CH₂)
\\O/

2.58–2.85

(br, 1H, —CH——CH₂)
\\O/

5.43–6.35 (m, 3H,

Si—C<u>H</u>=CH₂)

From the results of these analyses, it was verified that the obtained product was 5,6-epoxyhexyldimethyl-vinylsilane having the following structural formula.

CH₂——CH—(CH₂)₄Si(CH₃)₂(CH=CH₂)
\\O/

The yield to the theoretical yield was 63% based on (3-chloropropyl) dimethylvinylsilane.

Example 3

The reaction product showing a boiling point of 132° C./1 Torr was obtained in 193 parts in a manner similar to Example 1 except that 287 parts of (3-chloropropyl) diphenylvinylsilane was used in place of (chloromethyl) dimethylvinylsilane.

With the reaction product, identification was performed as in Example 1. The molecular weight of the reaction product by gas mass spectrum analysis, the results of elemental analysis, and IR and 1H-NMR spectra and their attribution are as shown in Table 3.

TABLE 3

| Molecular weight | 309 |
|---|---|
| Elemental analysis (%) | C 77.98 (77.87) |
| Figures with parenthesis indicate calculated values. | H 7.91 (7.84) |
| | Si 9.01 (9.10) |
| IR (liquid film method) | |
| ν (cm⁻¹) | 3040, 2935, 1428, 1115, 700 |
| ¹H—NMR | 0.40–0.65 |
| (90MHz; CCl₄) | (br, 2H, Si—C<u>H₂</u>—) |
| δ (ppm) | 1.10–1.60 |
| | (br, 6H, SiCH₂—C<u>H₂</u>—CH₂C<u>H₂</u>—) |
| | 2.18–2.60 |
| | (m, 2H, —CH——C<u>H₂</u>) \\O/ |
| | 2.60–2.93 |
| | (br, 1H, —C<u>H</u>——CH₂) \\O/ |
| | 5.42–6.37 (m, 3H, Si—C<u>H</u>=C<u>H₂</u>) |
| | 6.73–7.63 (m, 10H, |

TABLE 3-continued

Si(C₆H₅)₂)

From the results of these analyses, it was verified that the obtained product was 5,6-epoxyhexyl diphenylvinylsilane having the following structural formula.

CH₂——CH—(CH₂)₄Si(C₆H₅)₂(CH=CH₂)
\\O/

The yield to the theoretical yield was 63% based on (chloropropyl)diphenylvinylsilane.

Example 4

The reaction product showing a boiling point of 72° C./2.5 Torr was obtained in 119 parts in a manner similar to Example 1 except that 159 parts of (3-chloropropyl) methyldivinylsilane was used in place of (chloromethyl)dimethylvinylsilane.

The molecular weight of the reaction product by gas mass spectrum analysis, the results of elemental analysis, and IR and 1H-NMR spectra and their attribution are as shown in Table 4.

TABLE 4

| Molecular weight | 196 |
|---|---|
| Elemental analysis (%) | C 67.47 (67.27) |
| Figures with parenthesis indicate calculated values. | H 10.35 (10.26) |
| | Si 14.19 (14.30) |
| IR (liquid film method) | |
| ν (cm⁻¹) | 3040, 2935, 1245, 837 |
| ¹H—NMR | −0.01 (S, 3H, SiCH₃) |
| (90MHz; CCl₄) | 0.35–0.70 |
| δ (ppm) | (br, 2H, Si—C<u>H₂</u>—) |
| | 1.14–1.65 |
| | (br, 6H, SiCH₂—C<u>H₂</u>—CH₂C<u>H₂</u>—) |
| | 2.20–2.65 |
| | (m, 2H, —CH——C<u>H₂</u>) \\O/ |
| | 2.57–2.87 |
| | (br, 1H, —C<u>H</u>——CH₂) \\O/ |
| | 5.38–6.37 |
| | (m, 6H, Si(C<u>H</u>=C<u>H₂</u>)₂ |

From the results of these analyses, it was verified that the obtained product was 5,6-epoxyhexylmethyl-divinylsilane having the following structural formula.

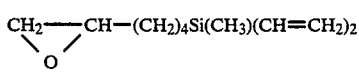

The yield to the theoretical yield was 61% based on (3-chloropropyl) methyldivinylsilane.

While the invention has been described in detail and with reference to specific embodiments thereof, it is apparent to one skilled in the art that various changes and modifications can be made therein without departing from the spirit and the scope of the present invention.

What is claimed is:

1. An epoxy-containing organic silicon compound represented by general formula (I):

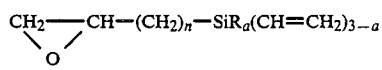

wherein R, which may be the same or different, represents a monovalent hydrocarbon group free from an aliphatic unsaturated bond which is selected from the group consisting of an alkyl group, a cycloalkyl group, an aryl group and an aralkyl group having up to 9 carbon atoms; a represents 1 or 2; and n represents an integer of 2 to 6.

2. An epoxy-containing organic silicon compound as claimed in claim 1, wherein said monovalent hydrocarbon group is an alkyl group or phenyl group.

3. An epoxy-containing organic silicon compound as claimed in claim 2, wherein said monovalent hydrocarbon group is methyl group.

4. An epoxy-containing organic silicon compound as claimed in claim 1, wherein a is 2.

* * * * *